(12) United States Patent
Naik et al.

(10) Patent No.: US 11,673,147 B2
(45) Date of Patent: Jun. 13, 2023

(54) AIR PURIFICATION SYSTEM

(71) Applicants: Praful Ramachandra Naik, Pune (IN); Alok Kumar Gupta, New Delhi (IN)

(72) Inventors: Praful Ramachandra Naik, Pune (IN); Alok Kumar Gupta, New Delhi (IN)

( * ) Notice: Subject to any disclaimer, the term of this patent is extended or adjusted under 35 U.S.C. 154(b) by 310 days.

(21) Appl. No.: 17/045,198

(22) PCT Filed: Mar. 4, 2019

(86) PCT No.: PCT/IB2019/051711
§ 371 (c)(1),
(2) Date: Oct. 5, 2020

(87) PCT Pub. No.: WO2019/193433
PCT Pub. Date: Oct. 10, 2019

(65) Prior Publication Data
US 2021/0039112 A1    Feb. 11, 2021

(30) Foreign Application Priority Data
Apr. 7, 2018    (IN) .............................. 201821013355

(51) Int. Cl.
*B03C 3/41* (2006.01)
*B03C 3/019* (2006.01)
(Continued)

(52) U.S. Cl.
CPC ................ *B03C 3/41* (2013.01); *B03C 3/019* (2013.01); *B03C 3/368* (2013.01); *B03C 3/47* (2013.01);
(Continued)

(58) Field of Classification Search
CPC combination set(s) only.
See application file for complete search history.

(56) References Cited

U.S. PATENT DOCUMENTS 2,505,907 A * 5/1950 Meston ...................... B03C 3/41
 72/66
3,819,985 A * 6/1974 Dusevoir .................. B03C 3/41
 96/96
(Continued)

FOREIGN PATENT DOCUMENTS

EP    1891982    2/2008
JP    2001038243 A *  2/2001 ............... B03C 3/41
(Continued)

*Primary Examiner* — Christopher P Jones
*Assistant Examiner* — Sonji Turner
(74) *Attorney, Agent, or Firm* — Sand, Sebolt & Wernow Co., LPA

(57) ABSTRACT

The present disclosure envisages an air purification system. The system comprises includes a shell, a blower, an electrode and a plurality of spikes. The shell has electrically-grounded wall(s), an inlet, and an outlet. The blower generates flow of air through the shell. The electrode is fitted within the shell between the inlet and the outlet and is electrically isolated from the shell body. The spikes extend from the electrode. The spikes have tips spaced apart from the inner surfaces of the walls and generate a corona between the tips and the inner surface of the walls when an high voltage electric current is passed through the electrode and thereby ionize gases and charge particles present in the air resulting in the particles being deposited on the inner surface of the walls of the shell.

16 Claims, 18 Drawing Sheets

(51) Int. Cl.
    *B03C 3/36*     (2006.01)
    *B03C 3/47*     (2006.01)
    *B03C 3/49*     (2006.01)
    *A61L 9/22*     (2006.01)

(52) U.S. Cl.
    CPC .................. *B03C 3/49* (2013.01); *A61L 9/22* (2013.01); *A61L 2209/14* (2013.01)

(56) References Cited

U.S. PATENT DOCUMENTS

| | | | | |
|---|---|---|---|---|
| 3,911,566 | A * | 10/1975 | Dusevoir | B03C 3/41 53/118 |
| 4,313,741 | A * | 2/1982 | Masuda | B03C 3/60 96/78 |
| 6,228,148 | B1 * | 5/2001 | Aaltonen | B01D 53/323 96/228 |
| 9,114,404 | B2 * | 8/2015 | Alam | B03C 3/60 |
| 2005/0028676 | A1 * | 2/2005 | Heckel | B03C 3/41 96/95 |
| 2008/0072759 | A1 * | 3/2008 | Podhorsky | B03C 3/14 96/100 |
| 2009/0151567 | A1 * | 6/2009 | Krigmont | B03C 3/09 96/66 |
| 2010/0089234 | A1 * | 4/2010 | Khoury | B03C 3/41 96/60 |
| 2011/0056376 | A1 * | 3/2011 | Pasic | B03C 3/41 96/97 |
| 2014/0102302 | A1 * | 4/2014 | Liu | B01D 53/925 96/84 |
| 2015/0050191 | A1 | 2/2015 | Li et al. | |
| 2019/0388903 | A1 * | 12/2019 | Vossoughi Khazaei | H05H 1/4645 |

FOREIGN PATENT DOCUMENTS

| | | | | |
|---|---|---|---|---|
| KR | 20170076939 A | * | 7/2017 | |
| WO | WO-2013010328 A1 | * | 1/2013 | ......... B01D 39/1676 |

\* cited by examiner

AIR PURIFICATION SYSTEM

TECHNICAL FIELD

The present disclosure relates to the field of air purification systems.

Definition

As used in the present disclosure, the following terms are generally intended to have the meaning as set forth below, except to the extent that the context in which they are used indicate otherwise.

Aerodynamic diameter: The expression 'aerodynamic diameter' used hereinafter in this specification refers to, but is not limited to, the diameter of an irregularly shaped particle with a density of 1000 kg/m$^3$ (i.e., that of water at 4° C.) and the same settling velocity as that of the irregularly shaped particle. In other words, aerodynamic diameter of an irregularly shaped particle is the diameter of a hypothetical spherical particle with the same aerodynamic behaviour as that of the given irregularly shaped particle. Aerodynamic diameter is conventionally expressed in micrometers, e.g. 'PM 10' refers to an aerodynamic diameter of 10 micrometer.

Corona: The expression 'corona' used hereinafter in this specification refers to, but is not limited to, an electrical discharge brought about by the ionization of molecules in a medium such as air surrounding a conducting element such as an electrode that is supplied with a substantially high voltage value.

Blower: The expression 'blower' used hereinafter in this specification refers to, but is not limited to, a device configured to generate flow of air through an enclosed space such as a duct. A fan, a blower, a turbine and similar devices fall under this definition.

BACKGROUND OF THE INVENTION

The background information herein below relates to the present disclosure but is not necessarily prior art.

Suspended particulate matters (SPM) present in the air, ranging from 0.01 microns to 50 microns, includes fine dust particles, exhaust gas particles, chimney smoke, industrial emissions, traffic emissions, domestic emissions (including centralized heating) and large smog particles. Such SPM causes undesirable health issues. The smaller the size of the SPM, the more difficult it becomes to filter it. SPM has been increasingly found to be associated with chronic cardiovascular, respiratory and neurological diseases which often lead to mortality.

A number of methods and systems for air filtration are known in the art. For instance, different types of filters (such as a centrifugal filter, a bag filter, a mesh filter, a leaf filter, a cloth filter, a carbon filter) are used to filter the air. However, such filters are not efficient as they fail to completely filter out the fine particles in the air, particularly particles below the size of 1 micron. Such fine particles are difficult to filter and are the main pollutants, causing respiratory issues.

Pollutant gases such as nitrogen oxides ($NO_x$), sulphur oxides ($SO_x$), hydrogen sulphide ($H_2S$), and the like cannot be filtered by the conventional means of air purification.

Odours resulting from various emissions also need treatment before the air can be circulated into interior spaces.

Another way for controlling solids and liquid aerosol concentration in the air is to pass the air through an electrostatic filter which induces a charge on the suspended particles in the air and then filters them out from the air. Such filters are very helpful in filtering out solids with particle sizes in the range of microns from the polluted air. However, such electrostatic filters operate at very high DC voltage, thereby forming significant amount of ozone gas.

Therefore, there is felt a need for an air purification system that alleviates the above-mentioned drawbacks.

OBJECT OF THE INVENTION

Some of the objects of the present disclosure, which at least one embodiment herein satisfies, are as follows:

An object of the present disclosure is to provide an air purification system which filters fine particles and coarse particles from the air.

Another object of the present disclosure is to provide an air purification system which removes the suspended particles from the air.

Yet another object of the present disclosure is to provide an air purification system which reduces gases such as $NO_x$, $SO_x$, $H_2S$ and odour emitted from chimney smoke, industrial emissions, traffic emissions and domestic emissions including central heating.

Yet another object of the present disclosure is to provide an air purification system which maintains the levels of ozone within permissible limits in the purified air by bringing the levels of ozone generated, if any, within the purification system within permissible limits.

Other objects and advantages of the present disclosure will be more apparent from the following description, which is not intended to limit the scope of the present disclosure.

SUMMARY OF THE INVENTION

The present disclosure envisages an air purification system. The air purification system comprises a tubular shell, a blower, an elongate electrode and a plurality of spikes. The tubular shell is defined by at least one electrically grounded wall defined by an inner surface and an outer surface, an inlet at one end and an outlet at the other end. The blower is configured to generate flow of air through the shell. The elongate electrode is fitted within the shell between the inlet and the outlet of the shell and is electrically isolated from the shell body. The plurality of spikes extends from the electrode. The spikes have tips spaced apart from the inner surfaces of the walls and are configured to generate a corona between the tips and the inner surface of the walls when an electric current of high voltage is made to pass through the electrode and thereby ionize gases and charge particles present in the air resulting in the particles being deposited on the inner surface of the walls of the shell.

In an embodiment, the spikes are provided along the length of the electrode in a spatially distributed manner.

In an embodiment, the electrode is an elongate strip of conductive material, wherein the spikes are formed on at least one edge of the strip. In another embodiment, the electrode is an elongate strip of conductive material, wherein the spikes are attached on at least one edge of the strip. The strip is twisted along its length through a predetermined angle with number of twists based on the electrode length, as a result of which the electrode forms a dual-helical corona therearound when an electric current of high voltage is made to pass through the electrode.

In yet another embodiment, the electrode is formed from a tube of conductive material by attaching the spikes on the external surface of the tube. In still another embodiment, the electrode is formed from a rod of conductive material by attaching the spikes on the external surface of the rod.

In an embodiment, the spikes are arranged in a spaced apart configuration.

The predetermined velocity of flow of air is in the range of 1 m/s-7 m/s. The predetermined twist angle across the electrode based on the electrode length is in the range of 5°-720°. In an embodiment, the predetermined voltage is in the range of 25000V-50000V. In another embodiment, the predetermined voltage is in the range of 3000V-15000V.

In an embodiment, the electrode is an elongate strip of conductive material with spikes formed on at least an edge of the strip. In another embodiment, the electrode is an elongate strip of conductive material with spikes attached on at least an edge of the strip. The strip is twisted along its length through a predetermined angle, as a result of which the electrode forms a dual-helical corona therearound, when supplied with the predetermined voltage. In yet another embodiment, the electrode is formed from a tube of conductive material by attaching the spikes on the external surface of the tube. In still another embodiment, the electrode is formed from a rod of conductive material by attaching the spikes on the external surface of the rod. Cross-section of the tube/the rod is selected from a group consisting of circular, oval, elliptical, regular polygonal and irregular polygonal.

In an embodiment, the shell comprises a plurality of electrodes and a plurality of internal walls defining a plurality of chambers with one chamber enclosing each electrode.

According to an aspect of the disclosure, adjacent spikes are separated by a predetermined distance of separation. In an embodiment, the predetermined distance of separation varies along the length of the electrode. The predetermined distance of separation preferably decreases along the length of the electrode towards the outlet of the shell.

In an embodiment, the system comprises a pre-filtration chamber. In another embodiment, the system comprises a post-filtration chamber.

BRIEF DESCRIPTION OF THE DRAWINGS

An air purification system of the present disclosure will now be described with the help of the accompanying drawing, in which.

LIST OF REFERENCE NUMERALS

Figure 1:
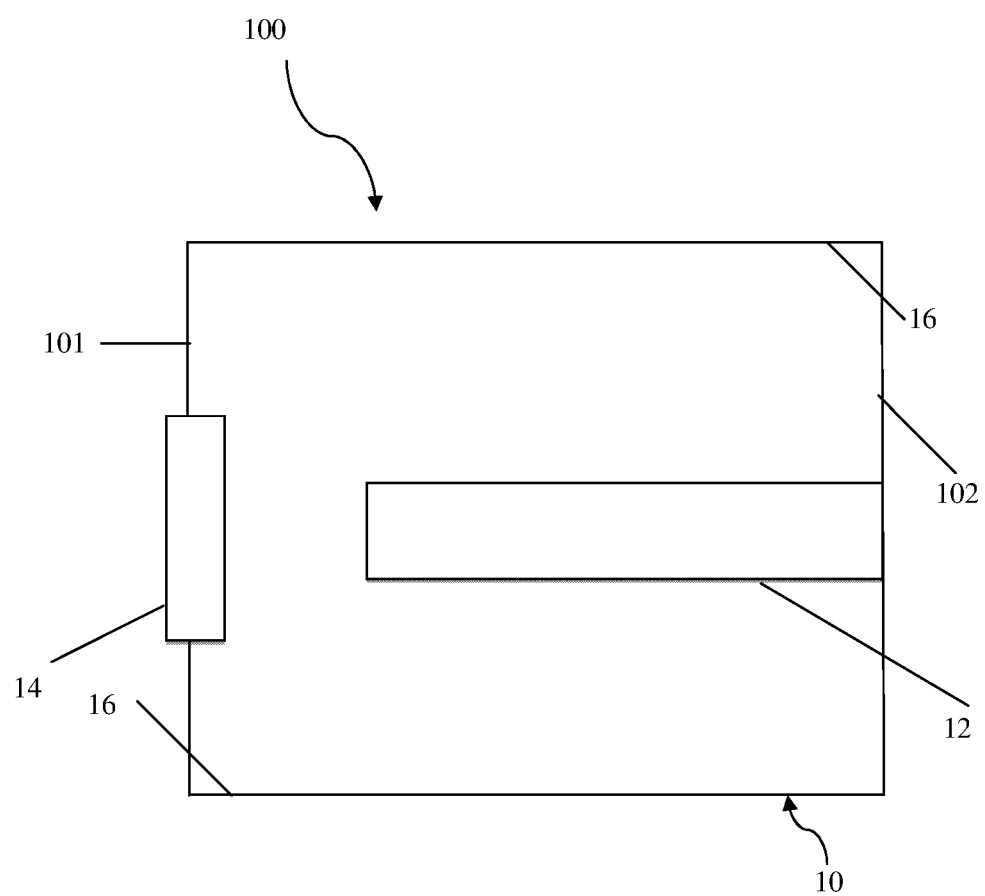
FIG. 1 is a schematic diagram of an air purification system of the present disclosure.

100 Air purification system
10 Shell
101 Inlet
111 louvre
102 Outlet
12 Electrode
122 Conducting strip/tube/rod
124 Spike
13 Chamber
14 Air flow generating device (ventilator)
16 Wall (precipitation plate)
16A Internal wall
18 Bracket
19 Holder
20 Pre-filtration chamber
30 Post-filtration chamber
C Corona
C' Dead zone
D Dust particle
E Electrode
P Precipitation plate
I Repulsion zone
II Transition zone
III Attraction zone
40 Power supply
45 Emergency switch
l Louvre width
d Louvre distance
α Louvre angle of attack

DETAILED DESCRIPTION

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a", "an" and "the" may be intended to include the plural forms as well, unless the context clearly suggests otherwise. The terms "comprise", "comprising", "including" and "having" are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

Currently known air purification systems for purifying air to be circulated inside enclosed spaces are known to eliminate particulate pollutants of aerodynamic diameters up to 10 microns. However, particulate pollutants of sizes below 1 micron remain mostly unfiltered. Also, $NO_x$, $SO_x$, $H_2S$ and similar other pollutants are also not treated by the conventional air filters. Hence, there is a need of an air purification system which primarily eliminates all particulate matter of very small sizes as well as treats the NO and SON content of the air up to a considerable extent.

The present disclosure envisages an air purification system 100 as illustrated in the schematic diagram of FIG. 1. The system 100 comprises a tubular shell 10 defined by at least one electrically grounded wall 16 and having an inner surface, an outer surface, an inlet 101 at one end and an outlet 102 at the other end, a blower 14, an elongate electrode 12 fitted between the inlet 101 and the outlet 102 of the shell 10 parallel to the direction of flow of air through the shell 10, and an electric voltage supply. The ends of electrode 12 are fitted on insulating mounts mounted on frames, the frames being fitted at the inlet 101 and the outlet 102. The insulating mounts are made of ceramic or similar other electrically insulating material. The blower 14 is configured to generate flow of air through the inlet 101 and the outlet 102. The electrode 12 is provided with a plurality of spikes 124 along its length. The spikes 124 have tips spaced apart from the inner surface. The electric voltage supply is configured to apply a predetermined voltage on the electrode 12 to make a predetermined electric current to pass through the electrode 12. The spikes 124 are configured to generate a corona between the tips and the inner surface of the walls 16 when the electric current passes through the electrode 12. As air flowing through the shell 10 interacts with the corona generated between the tips of the spikes 124, the gases contained therein are ionized and the particles of dust, dirt, and the like are charged resulting in deposition of the particles on the inner surface of the walls 16 of the shell 10.

According to an embodiment, the spikes 124 are provided along the length of the electrode 12 in a spatially distributed manner. As a result, when an electric current is made to pass through the electrode 12, the corona that is generated about the electrode 12 in the space within the shell 10 is distributed, as seen along the axis of the electrode 12.

Figure 2:
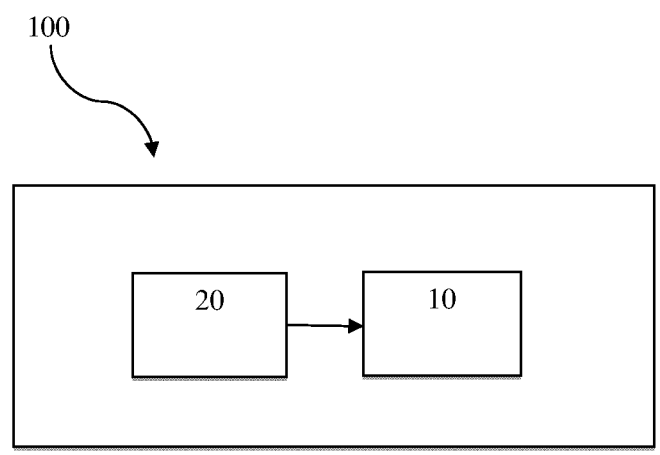
FIG. 2 is a schematic block diagram of an air purification system according to an embodiment of the present disclosure.

According to an embodiment illustrated by the schematic diagram of FIG. 2, a pre-filtration chamber 20, (at inlet side), is provided at the inlet 101 for eliminating coarse particulate matter above 30 µm from the ambient air being pulled into the system. In an embodiment, the pre-filtration chamber 20 is of cyclone, static, high-voltage, mechanical type.

Figure 3:
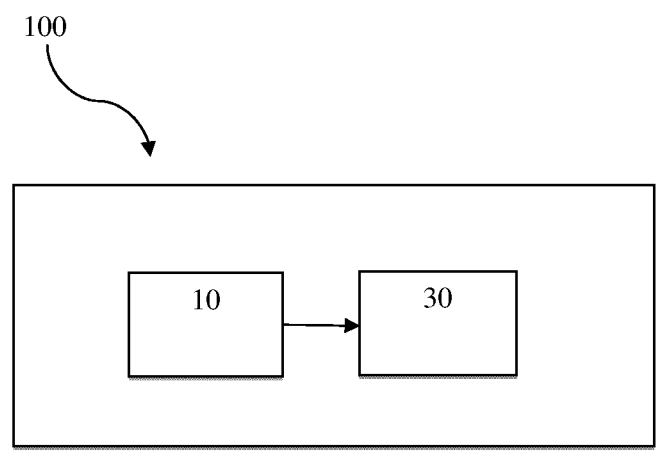
FIG. 3 is a schematic block diagram of an air purification system according to another embodiment of the present disclosure.

According to an embodiment illustrated by the schematic diagram of FIG. 3, a post-filtration chamber 30 is provided at the outlet 102 for removal of odour and gases from the treated and purified air.

Figure 4:
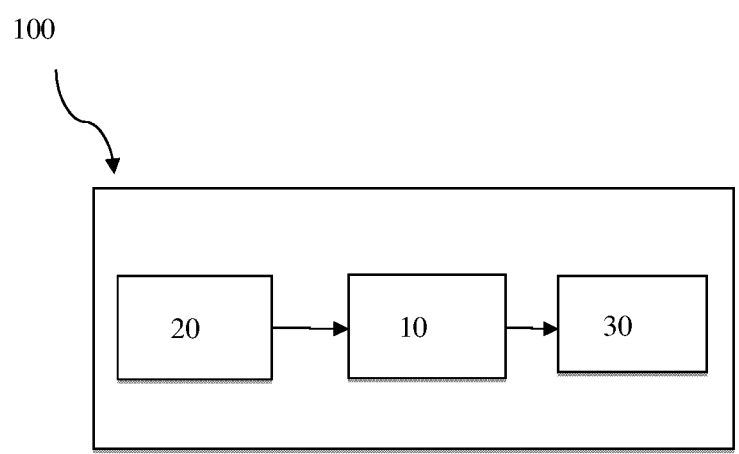
FIG. 4 is a schematic block diagram of an air purification system according to yet another embodiment of the present disclosure.

According to an embodiment illustrated by the schematic diagram of FIG. 4, a pre-filtration chamber 20 and a post-filtration chamber 30 are both provided to the system 100.

Figure 5:
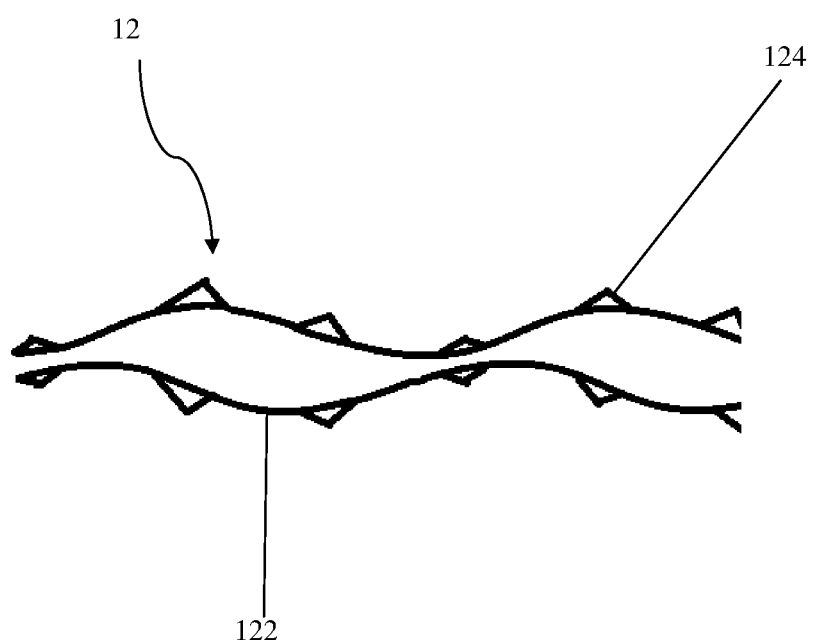
FIG. 5 is a side view of an electrode according to an embodiment of the present disclosure.
Figure 6:
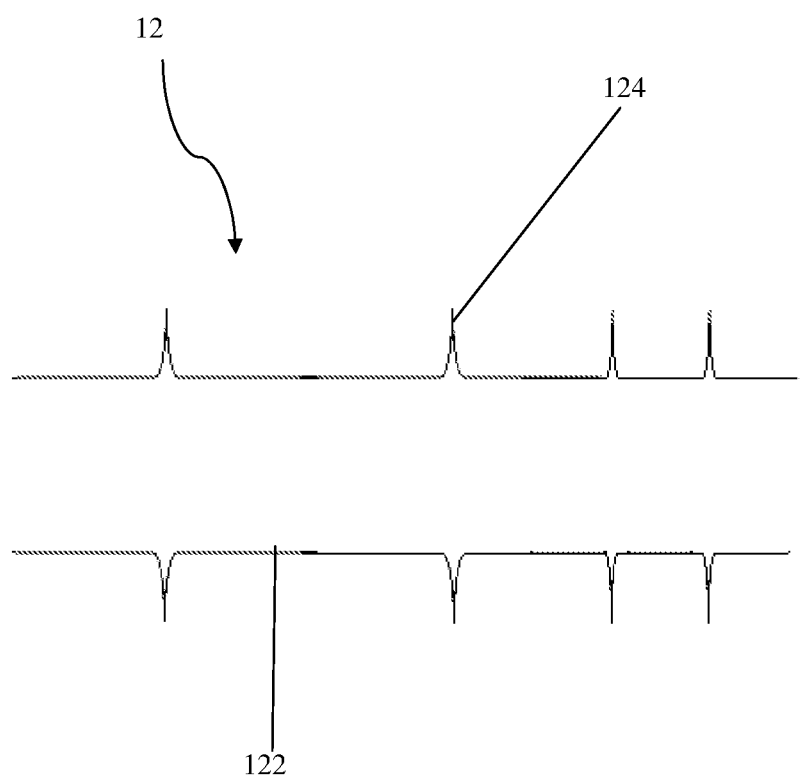
FIG. 6 is a side view of an untwisted electrode of FIG. 5 with variable spacing between adjacent spikes.

According to an embodiment, the electrode 12 is formed from an elongate strip 122 of conductive material provided with spikes 124 on at least an edge, as illustrated in FIG. 5 and FIG. 6. According to an embodiment, the spikes 124 are formed on at least an edge of the strip 122. According to another embodiment, the spikes 124 are externally attached on at least an edge of the strip 122. According to a yet another embodiment, the spikes 124 are attached in pairs, with a first spike on a top edge and a second spike on a bottom edge of the strip 122 right opposite to the first spike, as shown in FIG. 6. According to yet another embodiment, the spikes 124 are formed and/or attached in trios, with a first spike on a top edge of the strip, a second spike on a bottom edge of the strip, and a third spike on the surface of the strip. The electrode 12 thus obtained is twisted along its length through a predetermined angle in order to spatially distribute the spikes 124 about the electrode 12. The strip 122 has a length ranging from 1 metre to 5 metre and a width ranging from 15 mm to 40 mm. The thickness of the strip 122 is between 0.25 mm and 1.00 mm. According to an aspect of the present disclosure, the electrode 12 is installed such that the airflow through the shell 10 is parallel to the electrode 12. The electrode 12 is fitted to the walls of the inlet 101 and the outlet 102 of the shell 10 using holders 19 of Teflon or similar high voltage electrically insulating material. The electrode 12 is fitted on the holder 19 after giving specific number of twists based on the electrode length with the twist angle ranging from 5° to 720° across the length of the electrode 12, as shown in FIG. 5. The spikes 124, which are extended triangular projections on both sides along the thickness of the strip 122, have height ranging from 6 mm to 35 mm. According to another embodiment, the electrode 12 is formed from a tube 122 of conductive material by attaching the spikes 124 on the external and/or internal surface of the tube 122. Cross-section of the tube 122 is selected from a group consisting of circular, oval, elliptical, regular polygonal and irregular polygonal. According to another yet embodiment, the electrode 12 is formed from a rod 122 of conductive material by attaching the spikes 124 on the external surface of the rod 122. Cross-section of the rod 122 is selected from a group consisting of circular, oval, elliptical, regular polygonal and irregular polygonal. The spikes 124 are variably interspersed, with a predefined distance of separation in sets. According to another aspect of the present disclosure, the spikes 124 of the electrode 12 are placed closer, i.e., the distance of separation decreases, as the air moves towards the outlet 102, as shown in FIG. 6.

The air flow generating device 14, which is a ventilator 14 installed on the side of the inlet 101, comprises a waterproof and dust-proof fan for pulling/pushing ambient air into the system 100. The fan has a provision for speed adjustment to accomplish wind flow speed of ambient air pumped into the shell at 1-7 m/s. The air flow and cross-section of the shell 10 determine the air exchange capacity in cubic metres per hour ($m^3$/hr).

According to another embodiment, a ventilator is installed on the side of outlet 102 which is synchronized with the inlet ventilator. Further, the fans are rotated in opposite direction to avoid air turbulence inside the shell 10 and to enable consistency and uniformity of air flow speed across the length of the shell 10.

Figure 17:
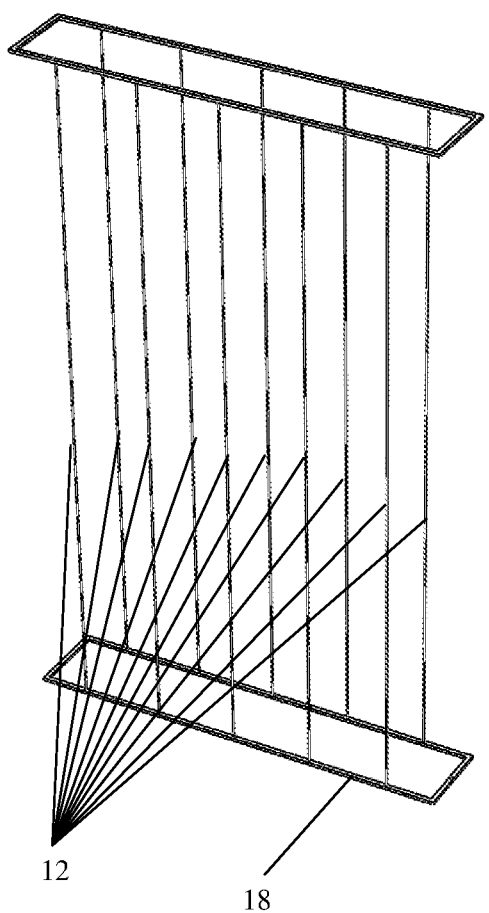
FIG. 17 illustrates a schematic diagram of an arrangement of multiple electrodes according to an embodiment of the present disclosure.

According to an embodiment, the system 100 is provided with multiple electrodes placed parallel to each other, as illustrated in FIG. 17. In another embodiment, multiple electrodes are placed in rows and columns with multiple electrodes parallel to each other in a row and parallel to the airflow. The distance of the walls 16 functioning as collector plates from the centre of the electrode 12 is within the range of 100-400 mm.

The working principle of the air purification system 100 is as follows. The polluted air is drawn by the ventilator fan 14 inside the shell 10 and the drawn-in air flows parallel to the electrode 12 fixed inside the shell 10. The electrode 12 has high-voltage DC current with voltage of 25,000V to 50,000V which enables break down and electric isolation of flowing air making it conductive. This phenomenon is called 'corona' or 'ionic wind'. The spikes 124 get positively charged. Molecules in air come into contact with these spikes. Air contains $N_2$ and $O_2$ along with other gases but $N_2$ and $O_2$ have the weakest valence electrons. The high-voltage current in the electrode provides the required energy to remove electrons from $N_2$ and $O_2$. The voltage is optimized for positive ionization to enable removal of only one electron and to avoid wastage of energy for removal of second electron from $N_2$ and $O_2$. The removal of electron from $N_2$ and $O_2$ leads to these molecules becoming positively charged. The removed electron because of its negative charge is attracted towards the electrode which is positive in charge. All electrons are attracted to the electrode as the distance traversed by these electrons is minimal. These electrons, while traversing, collide with other air molecules leading to creation of more positively charged ions. These positively charged ions created are in the vicinity of the electrode and therefore get repelled due to the positive charge of the electrode. The dust particles in the air are neutral and therefore there is attraction of the dust particles towards the positively charged ions. It takes about 0.1 to 1 sec for a dust particle to travel from the electrode to the wall acting as a collector plate at the defined wind flow speed and the defined distance of the walls acting as collector plates from the centre of the electrode. Based on the composition of elements in the dust particles it may require multiple ions to impact or break the dust particles' neutral status. As soon as the dust particle contacts the required number of positively charged ions the dust particle becomes positively charged and is repelled by the electrode leading to its movement away from the electrode towards the collector plates. During this movement, the positively charged dust particles attract surrounding suspended neutral dust particles binding together and sharing the positive charge, resulting in a chain reaction. As the collector plates are grounded, the positively charged dust particles go and adhere to the collector plates. When the dust particles adhere to the collector plates, they release their ions and become neutral again. However, the corona/ionic wind force being stronger than the flow of the air, it ensures that the dust particles settled/adhered to the collector plates remain stuck to the plates. The dust particles adhering to the collector plates bond with each other due to molecular force attraction converting the accumulated dust particles into coarse dust. The efficiency of the deposition of dust particles and accumulation of these particles depends on the chemical composition of the dust particles. Because of difference in resistance, a thickness from 1 mm to 20 mm of dust particles on the collector plates is achievable, thereby not requiring frequent cleaning of the collector plates.

At the same time, $NO_x$ and $SO_x$ contained in the air are converted to their elemental forms of $S_2$, $N_2$ and $O_2$ as their molecules pass through the corona/ionic wind. Hence, the air coming out of the outlet 102 has significantly reduced content of $NO_x$ and $SO_x$.

Figure 7:
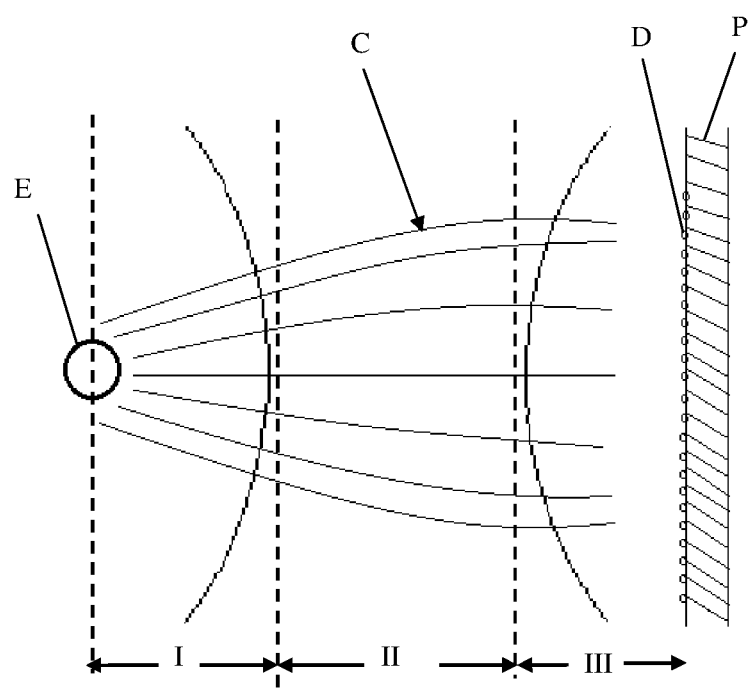
FIG. 7 is a representation of a corona formed between an electrode and a precipitation plate.

As shown in FIG. 7, the zone I of a corona C in the vicinity of an electrode E is a repulsion zone wherein positively charged molecules and particles in the air flowing therethrough get repelled away from the electrode E. Zone II of the corona C is a zone of transition from the repulsion-dominated zone I near the electrode E and the attraction-dominated zone III of the corona C near the collector plates P. The positively charged particles drift from zone I through the transition zone II and enter into the attraction zone III, where the grounded collector plate P attract them, and the particles D collect on the collector plate 16.

Figure 8:
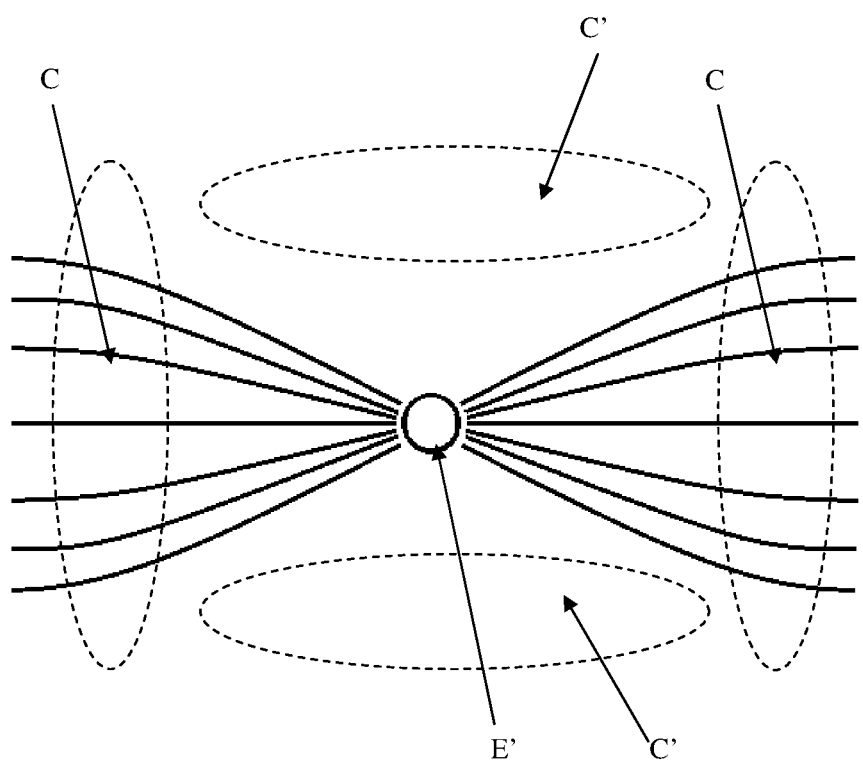
FIG. 8 is a representation of a corona around an untwisted electrode of prior art.
Figure 9:
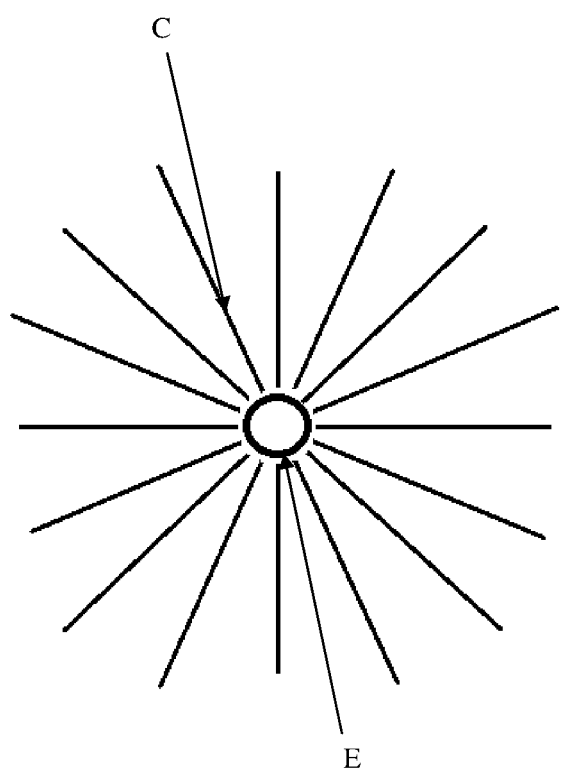
FIG. 9 is a representation of a corona around a twisted electrode of the present disclosure.

As seen through either the inlet 101 or the outlet 102 of the shell 10, the corona C is illustrated in FIG. 8 for an electrode E' of prior art with the spikes lying in a single plane parallel to the axis of the electrode E', and in FIG. 9 for an electrode E of the present disclosure with the spikes being spatially distributed about the axis of the electrode E. A largely bidirectional corona C is formed around the electrode E'. Dead zones C', i.e., zones within which no corona exists, is formed in this configuration of the electrode. Any particulate matter and other molecules contained in the air flowing through these dead zones remain unaffected by the corona. Hence, efficiency of filtration is rather low. On the other hand, by virtue of the spatial distribution of the spikes provided on the electrode E, which is an aspect of the present disclosure, the corona C is hypothetically formed at all the angles about the axis of the electrode E. The corona formation across the shell 10 of the present disclosure leads to significant reduction of nitrogen oxides and sulphur oxides. The $NO_x$ and $SO_x$ reduction accomplished by using an electrode such as the one shown in FIG. 5 is 50%-75% as compared to nil or negligible reduction of $NO_x$ and $SO_x$ by using an electrode with the spikes lying in a single plane.

According to another aspect of the present disclosure, the spikes 124 of the electrode 12 are placed closer, i.e., the distance of separation decreases, as the air moves towards the outlet 102, as shown in FIG. 6. As a result, the reach of the corona within the shell 10 is maintained, and the uniformity of the corona is enhanced along the length of the electrode 12 is enhanced towards the outlet of the shell 10 so as to ensure generation of ions and charged particles of $PM_4$ and below which are left unfiltered through the initial portion of the shell 10.

Figure 10A:
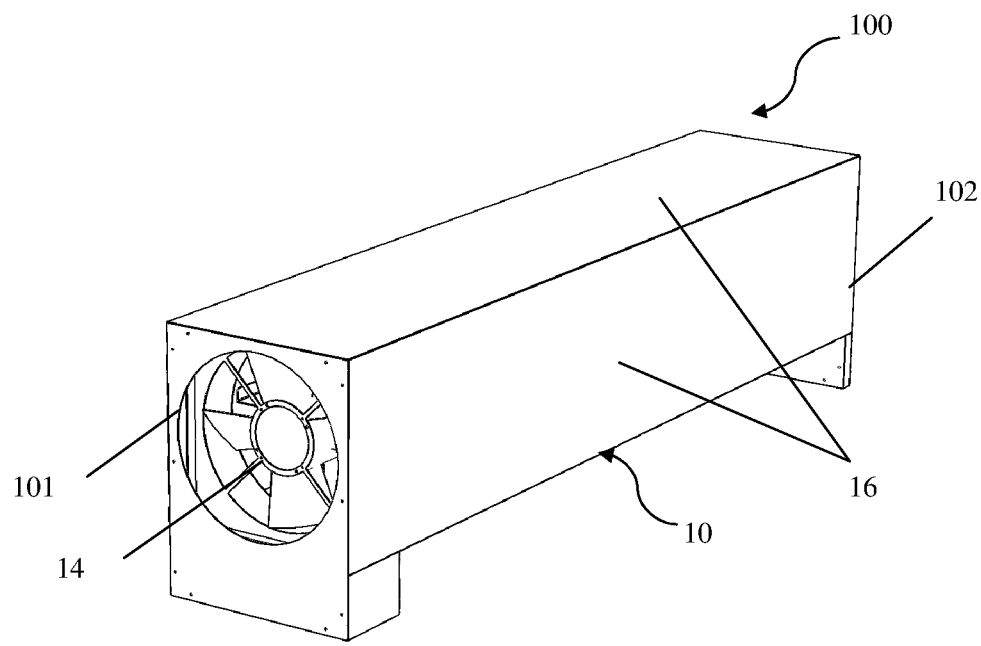
FIG. 10 illustrates an embodiment of the present disclosure.
Figure 10B:
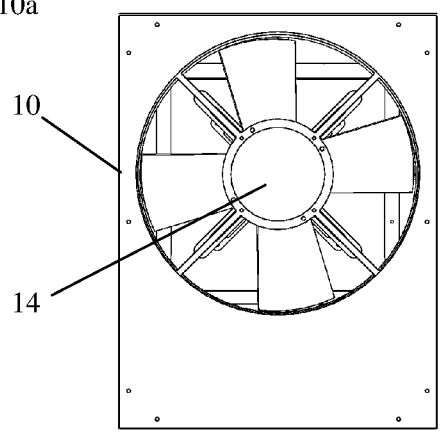
Figure 11A:
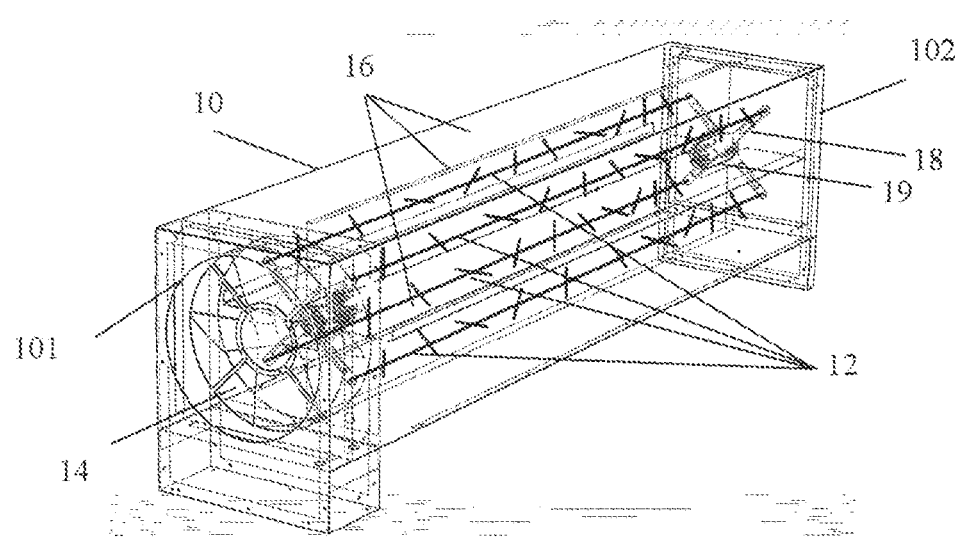
FIG. 11 illustrates transparent views of FIG. 10.
Figure 11B:
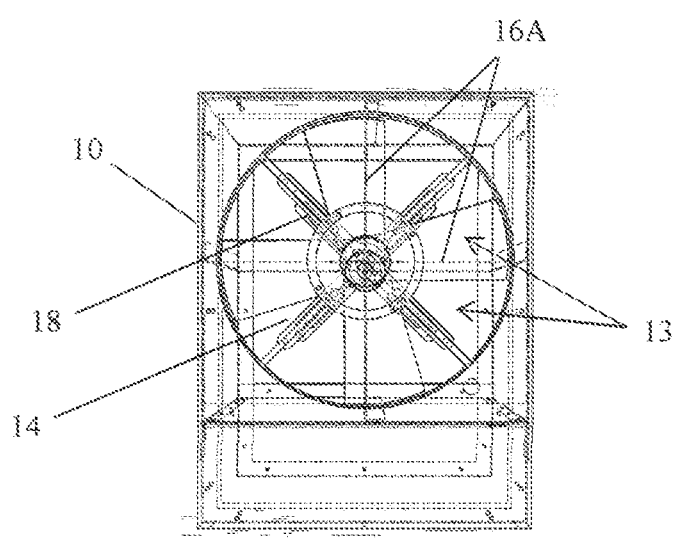

FIGS. 10-11 illustrate an embodiment of the present disclosure. The system 100 of FIGS. 10-11 comprises a shell 10 formed by walls 16—two operative external side walls, an operative top wall, an operative bottom wall and internal side walls. A fan 14 acting as an air flow generating device is installed at either longitudinal end of the shell 10. Four electrodes 12 of the present disclosure are installed between the inlet 101 and the outlet 102, as shown in the transparent view of FIG. 11a. Each electrode 12 is housed inside a chamber 13 and the chambers 13 are formed by inserting walls 16 within the shell 10 in a cross configuration. The electrodes 12 are mounted on ends of a bracket 18 and are electrically isolated from the shell 10 and the walls 16 by mounting, on one end of a Teflon or similar high voltage isolating material holder 19, the bracket 18, and on the other end, the internal walls 16A. In an embodiment, an air handling rate of 3500 m³/hr is a typical capacity for a system as illustrated in FIGS. 10-11. The 3500 m³/hr unit has at least one fan and optionally multiple fans, up to four fans. When provided with one fan, the mains power required is 230V/50 hz/1phase, the required power connection is 0.35 kW and the rated maximum speed of the fan is 1350 rpm. When provided with four fans, the mains power required is 230 VAC/50 hz/1phase, the required power connections are is 0.091 kW each and the rated maximum speed of each fan is 2650 rpm.

Figure 12A:
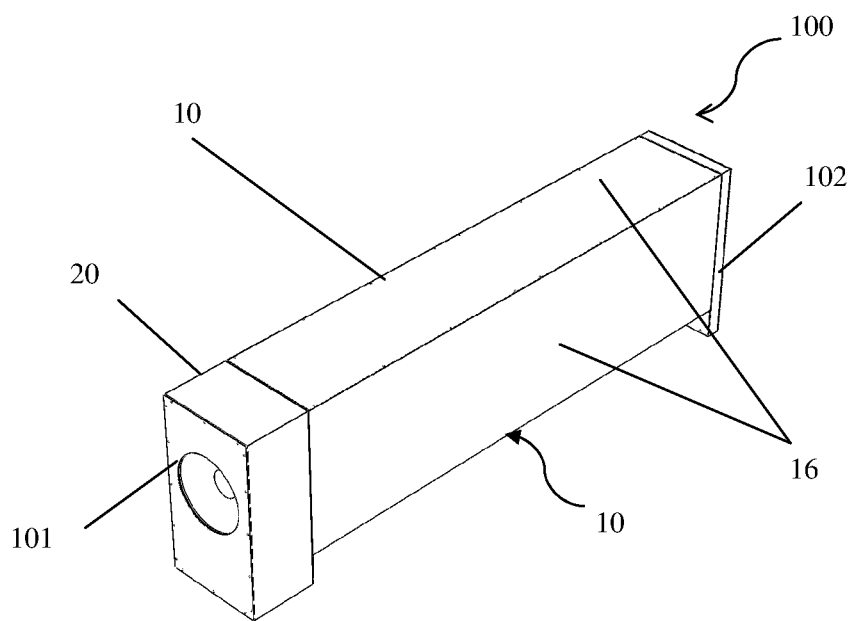
FIG. 12 illustrates another embodiment of the present disclosure.
Figure 12B:
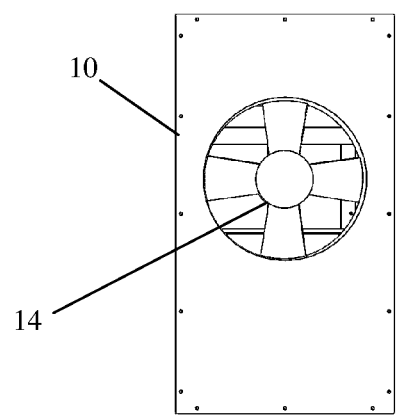
Figure 13A:
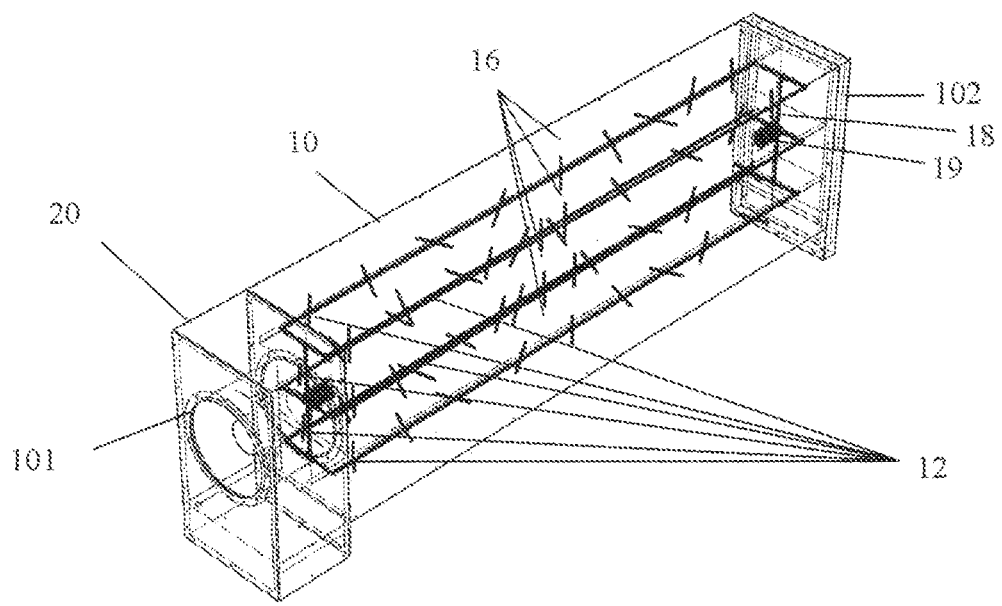
FIG. 13 illustrates transparent views of FIG. 12.
Figure 13B:
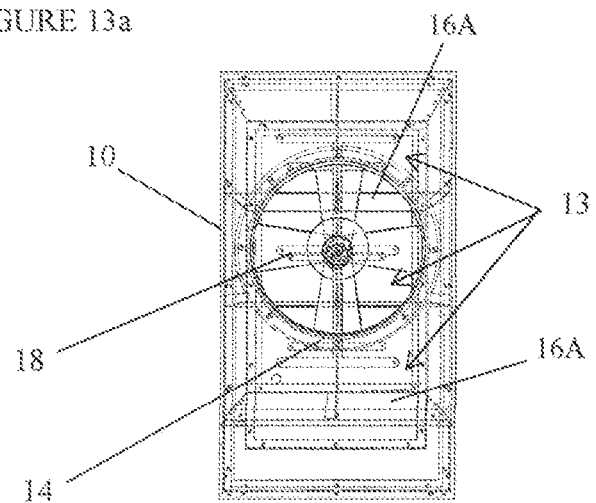

FIGS. 12-13 illustrate another embodiment of the present disclosure. The system 100 of FIGS. 10-11 comprises a shell 10 formed by walls 16—two vertical internal side walls, one vertical internal central wall, one horizontal internal upper wall, one horizontal internal lower wall, and two horizontal internal central walls, all walls being operative. A fan 14 acting as an air flow generating device is installed at either longitudinal end of the shell 10. Six electrodes 12 of the present disclosure are installed between the inlet 101 and the outlet 102, as shown in the transparent view of FIG. 13a. Each electrode 12 is housed inside a chamber 13. The chambers 13 are formed by inserting walls 16 within the shell 10 in a configuration in which one wall member is vertical and two wall members are horizontal, to form three two columns of chambers 13 with three chambers 13 in each column. The electrodes 12 are mounted on ends of a bracket 18 and are electrically isolated from the shell 10 and the walls 16 by mounting, on one end of a Teflon holder or similar high voltage isolating material 19, the bracket 18, and on the other end, the internal walls 16A. A pre-filtration chamber 20 is provided upstream of the shell 10. In an embodiment, an air handling rate of 6000 m³/hr is a typical capacity for a system as illustrated in FIGS. 12-13. The 6000 m³/hr unit has at least one fan and optionally multiple fans, up to six fans. When provided with one fan, the mains power required is 415V/50 hz/3phase, the required power connection is 0.37 kW and the rated maximum speed of the fan is 1450 rpm. When provided with four fans, the mains power required is 230 VAC/50 hz/1phase, the required power connections are is 0.091 kW each and the rated maximum speed of each fan is 2650 rpm.

Figure 14:
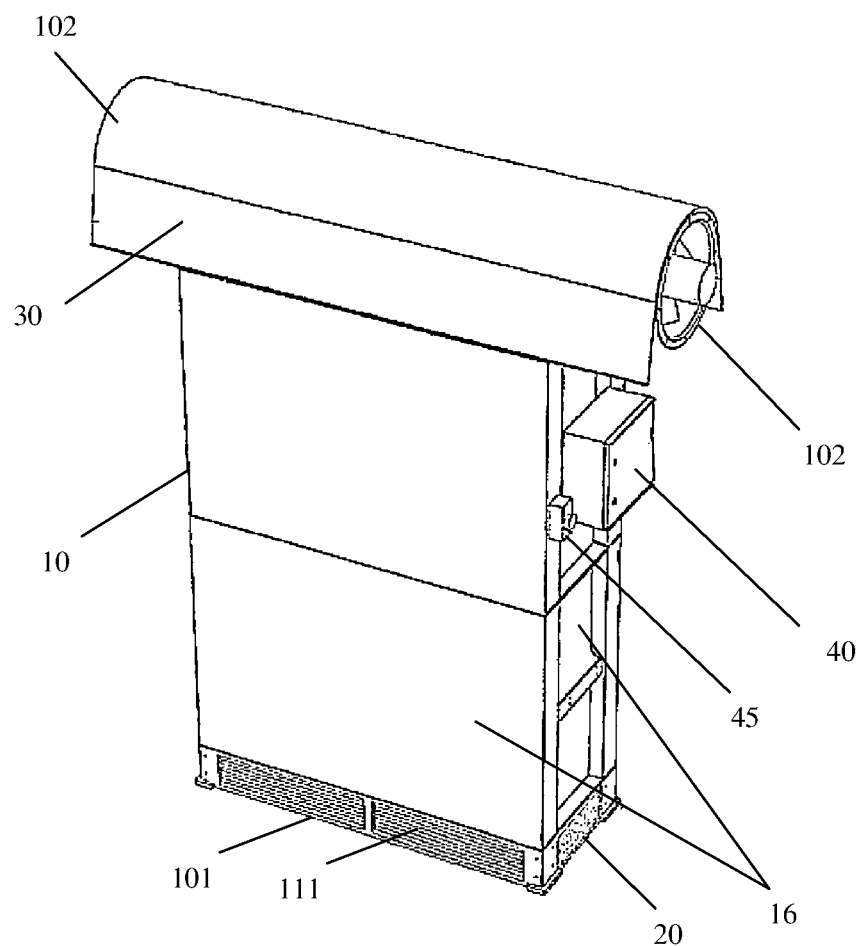
FIG. 14 illustrates yet another embodiment of the present disclosure.
Figure 15:
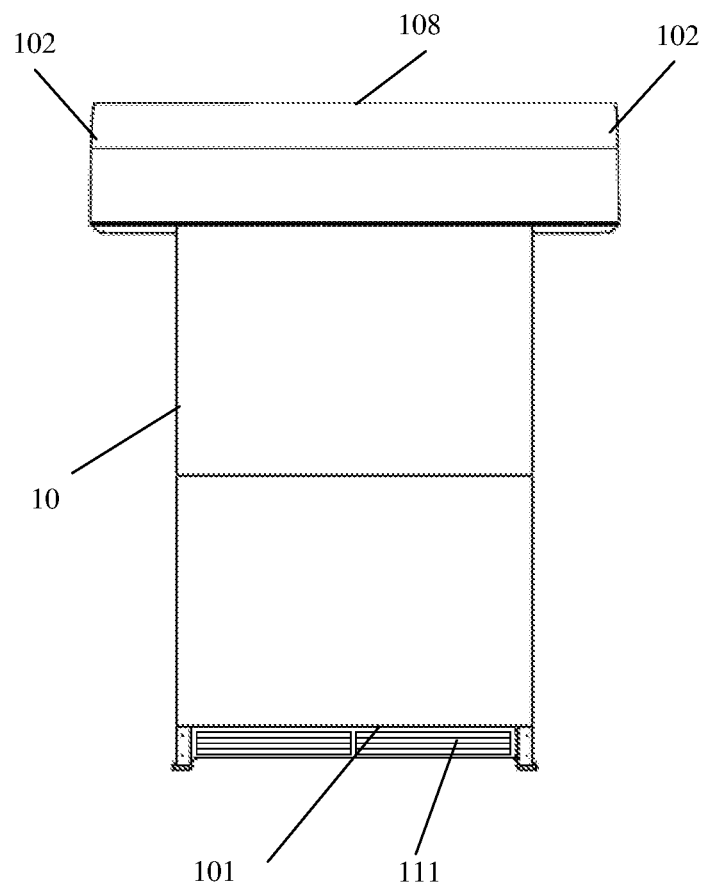
FIG. 15 illustrates a side view of the air purification system of FIG. 14.
Figure 16:
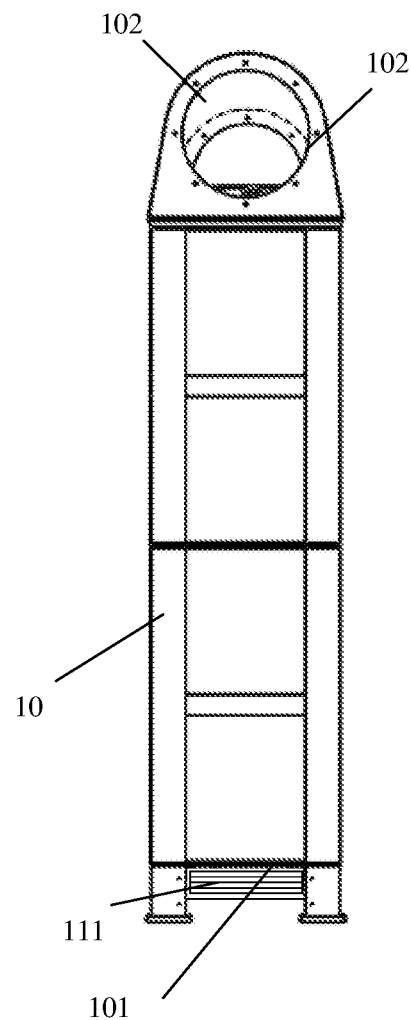
FIG. 16 illustrates a front view of the air purification system of FIG. 14.
Figure 18:
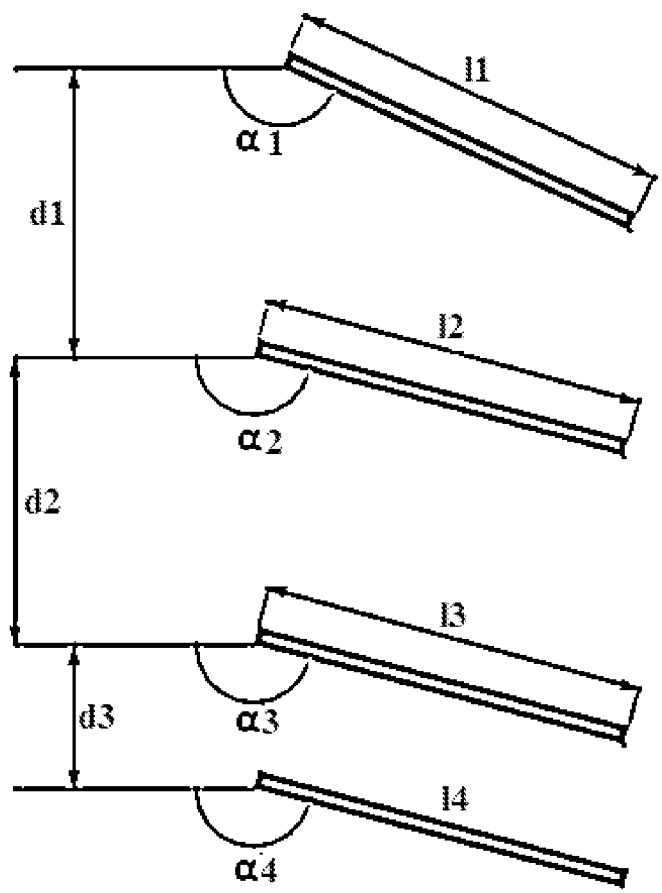
FIG. 18 shows variables concerned with louvres used in the system of FIG. 14.

FIGS. 14-16 illustrate yet another embodiment of the present disclosure. The system 100 of FIGS. 10-11 comprises a shell 10 formed by walls 16—four vertical external walls, four vertical walls parallel to the external lateral walls, and five vertical walls parallel to the external front and rear walls; All walls been operative. The inlet 101 is configured at the operative bottom end of the shell 10. A pre-filtration chamber 20 is installed at the inlet 101. At the operative top end of the shell 10, a plenum containing a post-filtration chamber 30 is installed. At least one fan 14 acting as an air flow generating device is installed at one longitudinal end of the plenum, thereby configuring an outlet 102. Ten electrodes 12 of the present disclosure, as illustrated in the schematic diagram of FIG. 17, are installed between the inlet 101 and the outlet 102. The electrodes 12 are mounted on ends of a bracket 18 and are electrically isolated from the shell 10 and the walls 16 by mounting, on one end of a Teflon holder or similar high voltage isolating material, the bracket 18, and on the other end, the internal walls 16A. In an embodiment, an air handling rate of 12000 m³/hr is a typical capacity for a system as illustrated in FIGS. 14-16. In an embodiment as illustrated in FIG. 14 and FIG. 15, the pre-filtration chamber has louvres 111 on all four sides. The number of louvres 111 on each side ranges from 5 to 20. The width (l) of each louvre ranges from 15 mm to 50 mm, distance (d) between each louvre ranges from 10 mm to 30 mm and louvre angle of attack ($\alpha$) ranges from 5° to 20°. In an embodiment, the width (l) of the louvres, the distance (d) between the louvres and the louvre angle of attack ($\alpha$) is variable between the louvres, as illustrated in FIG. 18. The louvres 111 are provided for ensuring that the air flowing in horizontally in the inlet 101 and undergoing a change in direction as it flows vertically upwards inside the shell 10 does not develop any turbulence. The louvres 111 and the mesh filters are optionally coated with titanium oxide to facilitate killing of bacteria and other organisms present in the ambient air. The 12000 m³/hr unit has at least one fan and optionally multiple fans. When provided with two fans, the mains power required is 415 VAC/50 hz/3phase, the required power connections are is 0.37 kW each and the rated maximum speed of each fan is 1450 rpm.

According to an embodiment, direct current (DC) with voltage ranging from 25,000V to 50,000V is applied to the electrode by means of the electric power supply 40. High-voltage positive polarity DC is preferred over high-voltage negative polarity DC to avoid inconsistent sparks and inconsistent magnitude of the corona. DC also gives significant cost advantage. However, alternating current (AC) can also be used. The power supply unit 40 is provided in combination with switch breakers and a PLC, i.e., programmable logic controller for the sensors placed inside the air purification system to detect the complete closure of the panels of the chambers 13 the inside of which form the particulate matter collector plates and hence cut-off power supply in case of non-closure of the panels. The number of sensors inside the system range from 4 to 20 depending on the size of the treatment chambers 13. There are sensors for the air suction and blower system to ensure indication of proper working of the system. According to another embodiment, the power supply unit 40 supplies high voltage DC with dual output with the first power supply output capable of 0V to 40,000V and the second power supply output capable of 0V to 12,000V, wherein the first power supply output is configured to charge the electrodes 12 and the second power supply output is configured to charge pre-filtration chamber 20 and/or post-filtration chamber 30. According to an embodiment, the system 100 is also provided with an emergency switch 45. The manually operable emergency switch 45, shown in FIG. 14, is used to turn the system 100, particularly the supply from the power supply unit 40, completely OFF, in order to avoid any safety hazard in an event such as accidental opening of the walls 16 of the shell 10, accidental entry of a living being such as a small pet or a bird inside the shell 10 and so on.

According to an embodiment, the threshold drop in efficiency is optionally monitored by use of two sensors, one at the outlet 102 and another at the inlet 101 which measures the particulate matter content of the out-flowing and in-flowing air and provide signals by means of sound/light indicator/alarm requiring stoppage of the purification process and cleaning of walls 16 acting as collector plates. According to another embodiment, a sensor which monitors the thickness of accumulated dust particles on the walls 16 acting as collector plates is configured which provides an indication of requirement of stoppage of the purification process and cleaning of the walls 16 acting as collector plates.

The shell 10 of the present disclosure is made from conductive material selected from a group consisting of stainless steel of the type SS302/304/316, brass, copper, galvanized steel, zinc-coated steel, titanium or an alloy made from these metals, or even conductive textile and/or composite materials. Walls 16 of the shell 10 are openable with the joints or partitions between the walls 16 being waterproof. The electrode 12 is made from material selected from a group consisting of stainless steel of type SS302/304/316, brass, copper, galvanized steel, zinc-coated steel, titanium or an alloy made from these metals which may be coated with grapheme-based product. Also, the electrode 12 can also be made from composite materials. Composite materials are highly conductive with very a low electrical resistance which enhances the efficiency significantly resulting from a better flow and more intense corona, enabling enhanced removal of particulate matter which can be as high as 30-50% more than a system having an electrode made from metals only.

The pre-filtration chamber 20 has a height ranging from 100 mm to 300 mm. The pre-filtration chamber 20 has a fixed or a removable mesh filter, optionally, multiple mesh filters made from SS304, SS316, copper or a copper alloy. Copper/copper alloy-based mesh filters enable better reduction of ozone present in the ambient air. The mesh is made from wire of diameter ranging from 0.01 mm to 0.5 mm with each hole having dimensions of 10 mm×10 mm. The hole dimensions are in the range from 5 mm to 100 mm.

The post-filtration chamber 30 comprises of a plenum which houses the air flow generating device 14. The post-filtration chamber 30 has either a single opening or multiple openings with at least one air flow generating device 14. A typical design of 12000 $m^3$/hr system illustrated in FIG. 14 has two air flow generating devices 14 where the fans rotate in the same or in opposite directions. The blades of the fans are optionally coated with titanium oxide for effective elimination of bacteria and other microorganisms in the purified air leaving the shell 10. The post-filtration chamber 30 has optionally titanium oxide coated mesh filters. The post-filtration chamber 30 optionally houses UV light system at 180 nm to 250 nm for effective elimination of bacteria and other microorganisms. The post-filtration chamber 30 optionally has active carbon mesh filters for removal of gases and odour from the purified air leaving the shell 10.

Cleaning of the dust collected on collector plates is accomplished by manual mechanical means using scrappers made of a suitable metal or of a hard polymeric material. The collector plates, which are walls of the shell, are either removed from the shell and cleaned or they are kept fixed within the shell and cleaned manually by scrappers. Automated cleaning devices can be installed within the shell 10 utilizing one of vibratory method, percussion method, ultrasonic method, scrapping, $CO_2$, liquid jets for either intermittent or a continuous cleaning process or cleaning-in-place process. Decision of incorporation of automated devices/processes is based on the cost analysis.

According to an embodiment, an ozone treatment device is installed for breaking of any ozone generated inside the shell 10 during removal of dust particles form the flowing air. This is accomplished by installation of ultraviolet light of 360-415 nm wavelength near the electrode 12, or by means of incorporating copper, titanium dioxide or active carbon filters within the shell 10 or at the outlet 102 of the shell 10.

According to another embodiment, a mist generator is incorporated within the shell 10 or at the outlet 102 of the shell 10 for either removal or addition of fragrance which may include herbal compositions.

Test results and inference:

Experimental tests were performed for validating the performance of three different embodiments of the air purification system of the present disclosure. A number of tests were conducted on 3500 $m^3$/hr, 6000 $m^3$/hr and 12000 $m^3$/hr capacity air purification units of the present disclosure. The sampling of particular matter of size-range of 10 micrometer, sulphur dioxide ($SO_2$), nitrogen dioxide ($NO_2$) and Ozone ($O_3$) was done as per IS 5182 standard, and sampling of particular matter of size-range of 2.5 micrometer was done as per CPCB guidelines. Measurements were taken over varying periods of running of the air purification system.

For sampling of air for monitoring of particulate matter, one measurement station each was kept near the inlet 101 and the outlet 102 of the purification system 100. Both stations sucked air at a constant velocity. Each measurement station had a cyclone which separates $PM_{2.5}$ and $PM_{10}$ where the $PM_{2.5}$ is diverted into a tube with a pad filter and the $PM_{10}$ goes to another tube having another pad filter.

After the stipulated period of running, the stations were stopped and the pads were taken to a laboratory for quantitative analysis by gravimetric measurement.

Hand-held particle counters were also used to monitor the particulate matter.

Results of the tests are tabulated below. The effectiveness of an electrode of the present disclosure is evident from the following tabular data.

I] Test results for 3500 $m^3$/hr air purification system:
Test 1:
Timing: 11:00 AM to 01:00 PM
Date: 24 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 320.5 | 186 | $\mu g/m^3$ | 42% |
| 2 | Particulate Matter ($PM_{2.5}$) | CPCB Guidelines, May 2011 | 112 | 68 | $\mu g/m^3$ | 39% |
| 3 | Sulphur di-oxide ($SO_2$) | IS: 5182, Part 2-2001 | 6.2 | 3.9 | $\mu g/m^3$ | 37% |
| 4 | Nitrogen di-oxide ($NO_2$) | IS: 5182, Part 6-2006 | 15.2 | 8.7 | $\mu g/m^3$ | 43% |
| 5 | Ozone ($O_3$) | IS: 5182, Part 9 | 0.04 | 0.045 | ppm | −13% |

Test 2:
Timing: 02:00 PM to 04:00 PM
Date: 24 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 226 | 101 | $\mu g/m^3$ | 55% |
| 2 | Particulate Matter ($PM_{2.5}$) | CPCB Guidelines, May 2011 | 86 | 43 | $\mu g/m^3$ | 50% |
| 3 | Sulphur di-oxide ($SO_2$) | IS: 5182, Part 2-2001 | 4.2 | 2.6 | $\mu g/m^3$ | 38% |
| 4 | Nitrogen di-oxide ($NO_2$) | IS: 5182, Part 6-2006 | 9 | 5.1 | $\mu g/m^3$ | 43% |
| 5 | Ozone ($O_3$) | IS: 5182, Part 9 | 0.023 | 0.026 | ppm | −13% |

Test 3:
Timing: 05:00 PM to 07:00 PM
Date: 24 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 328 | 112 | $\mu g/m^3$ | 66% |
| 2 | Particulate Matter ($PM_{2.5}$) | CPCB Guidelines, May 2011 | 125 | 65 | $\mu g/m^3$ | 48% |
| 3 | Sulphur di-oxide ($SO_2$) | IS: 5182, Part 2-2001 | 4 | 2.4 | $\mu g/m^3$ | 40% |
| 4 | Nitrogen di-oxide ($NO_2$) | IS: 5182, Part 6-2006 | 36 | 18.7 | $\mu g/m^3$ | 48% |
| 5 | Ozone ($O_3$) | IS: 5182, Part 9 | 0.032 | 0.037 | ppm | −16% |

Test 4:
Timing: 08:00 PM to 10:00 PM
Date: 24 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 340 | 105 | $\mu g/m^3$ | 69% |
| 2 | Particulate Matter ($PM_{2.5}$) | CPCB Guidelines, May 2011 | 124 | 56 | $\mu g/m^3$ | 55% |
| 3 | Sulphur di-oxide ($SO_2$) | IS: 5182, Part 2-2001 | 5.7 | 3.1 | $\mu g/m^3$ | 46% |
| 4 | Nitrogen di-oxide ($NO_2$) | IS: 5182, Part 6-2006 | 31 | 17.4 | $\mu g/m^3$ | 44% |
| 5 | Ozone ($O_3$) | IS: 5182, Part 9 | 0.04 | 0.045 | ppm | −13% |

Test 5:
Timing: 08:00 AM to 12:00 PM
Date: 25 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 152 | 64 | $\mu g/m^3$ | 58% |
| 2 | Particulate Matter ($PM_{2.5}$) | CPCB Guidelines, May 2011 | 59 | 32 | $\mu g/m^3$ | 46% |
| 3 | Sulphur di-oxide ($SO_2$) | IS: 5182, Part 2-2001 | 8.2 | 4.8 | $\mu g/m^3$ | 41% |
| 4 | Nitrogen di-oxide ($NO_2$) | IS: 5182, Part 6-2006 | 18 | 10 | $\mu g/m^3$ | 44% |
| 5 | Ozone ($O_3$) | IS: 5182, Part 9 | 0.021 | 0.023 | ppm | −10% |

Test 6:
Timing: 02:00 PM to 6:00 PM
Date: 25 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 145 | 46 | $\mu g/m^3$ | 68% |
| 2 | Particulate Matter ($PM_{2.5}$) | CPCB Guidelines, May 2011 | 52 | 22 | $\mu g/m^3$ | 58% |
| 3 | Sulphur di-oxide ($SO_2$) | IS: 5182, Part 2-2001 | 14 | 7.8 | $\mu g/m^3$ | 44% |
| 4 | Nitrogen di-oxide ($NO_2$) | IS: 5182, Part 6-2006 | 10 | 5.4 | $\mu g/m^3$ | 46% |
| 5 | Ozone ($O_3$) | IS: 5182, Part 9 | 0.021 | 0.0234 | ppm | −11% |

Test 7:
Timing: 08:00 PM to 12:00 AM
Date: 25 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 120 | 33.6 | $\mu g/m^3$ | 72% |
| 2 | Particulate Matter ($PM_{2.5}$) | CPCB Guidelines, May 2011 | 52 | 18.7 | $\mu g/m^3$ | 64% |
| 3 | Sulphur di-oxide ($SO_2$) | IS: 5182, Part 2-2001 | 11 | 6.2 | $\mu g/m^3$ | 44% |
| 4 | Nitrogen di-oxide ($NO_2$) | IS: 5182, Part 6-2006 | 16.4 | 9.6 | $\mu g/m^3$ | 41% |
| 5 | Ozone ($O_3$) | IS: 5182, Part 9 | 0.02 | 0.0234 | ppm | −17% |

Test 8:
Timing: 06:00 AM to 06:00 PM
Date: 26 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 115 | 25.3 | $\mu g/m^3$ | 78% |
| 2 | Particulate Matter ($PM_{2.5}$) | CPCB Guidelines, May 2011 | 41 | 11.9 | $\mu g/m^3$ | 71% |
| 3 | Sulphur di-oxide ($SO_2$) | IS: 5182, Part 2-2001 | 25.9 | 10.6 | $\mu g/m^3$ | 59% |
| 4 | Nitrogen di-oxide ($NO_2$) | IS: 5182, Part 6-2006 | 12 | 5.16 | $\mu g/m^3$ | 57% |
| 5 | Ozone ($O_3$) | IS: 5182, Part 9 | 0.0354 | 0.0397 | ppm | −12% |

Test 9:
Timing: 07:00 PM to 07:00 AM
Date: 26-27 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 103 | 16.5 | $\mu g/m^3$ | 84% |
| 2 | Particulate Matter ($PM_{2.5}$) | CPCB Guidelines, May 2011 | 45 | 9.9 | $\mu g/m^3$ | 78% |
| 3 | Sulphur di-oxide ($SO_2$) | IS: 5182, Part 2-2001 | 21.7 | 8.0 | $\mu g/m^3$ | 63% |
| 4 | Nitrogen di-oxide ($NO_2$) | IS: 5182, Part 6-2006 | 19.0 | 7.4 | $\mu g/m^3$ | 61% |
| 5 | Ozone ($O_3$) | IS: 5182, Part 9 | 0.0356 | 0.039 | ppm | −10% |

Test 10:
Timing: 08:00 AM to 08:00 PM
Date: 27 Feb. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 200 | 36 | $\mu g/m^3$ | 82% |
| 2 | Particulate Matter ($PM_{2.5}$) | CPCB Guidelines, May 2011 | 52 | 9.9 | $\mu g/m^3$ | 81% |
| 3 | Sulphur di-oxide ($SO_2$) | IS: 5182, Part 2-2001 | 7 | 2.2 | $\mu g/m^3$ | 69% |
| 4 | Nitrogen di-oxide ($NO_2$) | IS: 5182, Part 6-2006 | 19 | 6.5 | $\mu g/m^3$ | 66% |
| 5 | Ozone ($O_3$) | IS: 5182, Part 9 | 0.034 | 0.0384 | ppm | −13% |

II] Test results for 6000 m³/hr air purification system:

Test 1:
Timing: 08:00 AM to 10:00 AM
Date: 2 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 246 | 132.8 | $\mu g/m^3$ | 46% |
| 2 | Particulate Matter ($PM_{2.5}$) | CPCB Guidelines, May 2011 | 111 | 64.4 | $\mu g/m^3$ | 42% |
| 3 | Sulphur di-oxide ($SO_2$) | IS: 5182, Part 2-2001 | 2.9 | 1.8 | $\mu g/m^3$ | 38% |
| 4 | Nitrogen di-oxide ($NO_2$) | IS: 5182, Part 6-2006 | 35 | 19 | $\mu g/m^3$ | 46% |
| 5 | Ozone ($O_3$) | IS: 5182, Part 9 | 0.0094 | 0.0105 | ppm | −12% |

Test 2:
Timing: 01:00 PM to 03:00 PM
Date: 2 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 110 | 57.2 | $\mu g/m^3$ | 48% |
| 2 | Particulate Matter ($PM_{2.5}$) | CPCB Guidelines, May 2011 | 61 | 33.5 | $\mu g/m^3$ | 45% |
| 3 | Sulphur di-oxide ($SO_2$) | IS: 5182, Part 2-2001 | 4.2 | 2.4 | $\mu g/m^3$ | 43% |
| 4 | Nitrogen di-oxide ($NO_2$) | IS: 5182, Part 6-2006 | 11 | 6 | $\mu g/m^3$ | 45% |
| 5 | Ozone ($O_3$) | IS: 5182, Part 9 | 0.011 | 0.012 | ppm | −9% |

Test 3:
Timing: 04:00 PM to 06:00 PM
Date: 2 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 105 | 50.4 | $\mu g/m^3$ | 52% |
| 2 | Particulate Matter ($PM_{2.5}$) | CPCB Guidelines, May 2011 | 43 | 22.4 | $\mu g/m^3$ | 48% |
| 3 | Sulphur di-oxide ($SO_2$) | IS: 5182, Part 2-2001 | 5 | 2.8 | $\mu g/m^3$ | 44% |
| 4 | Nitrogen di-oxide ($NO_2$) | IS: 5182, Part 6-2006 | 9 | 4.8 | $\mu g/m^3$ | 47% |
| 5 | Ozone ($O_3$) | IS: 5182, Part 9 | 0.01 | 0.0112 | ppm | −12% |

Test 4:
Timing: 07:00 PM to 9:00 PM
Date: 2 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 134 | 56.3 | $\mu g/m^3$ | 58% |
| 2 | Particulate Matter ($PM_{2.5}$) | CPCB Guidelines, May 2011 | 44 | 20.24 | $\mu g/m^3$ | 54% |
| 3 | Sulphur di-oxide ($SO_2$) | IS: 5182, Part 2-2001 | 2 | 1 | $\mu g/m^3$ | 50% |
| 4 | Nitrogen di-oxide ($NO_2$) | IS: 5182, Part 6-2006 | 27 | 13 | $\mu g/m^3$ | 52% |
| 5 | Ozone ($O_3$) | IS: 5182, Part 9 | 0.0113 | 0.013 | ppm | −15% |

Test 5:
Timing: 08:00 AM to 12:00 PM
Date: 3 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 200 | 70 | $\mu g/m^3$ | 65% |
| 2 | Particulate Matter ($PM_{2.5}$) | CPCB Guidelines, May 2011 | 75 | 31.5 | $\mu g/m^3$ | 58% |
| 3 | Sulphur di-oxide ($SO_2$) | IS: 5182, Part 2-2001 | 8.2 | 4 | $\mu g/m^3$ | 51% |
| 4 | Nitrogen di-oxide ($NO_2$) | IS: 5182, Part 6-2006 | 20 | 9 | $\mu g/m^3$ | 55% |
| 5 | Ozone ($O_3$) | IS: 5182, Part 9 | 0.021 | 0.023 | ppm | −10% |

Test 6:
Timing: 02:00 PM to 6:00 PM
Date: 3 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 130 | 41.6 | $\mu g/m^3$ | 68% |
| 2 | Particulate Matter ($PM_{2.5}$) | CPCB Guidelines, May 2011 | 40 | 16 | $\mu g/m^3$ | 60% |
| 3 | Sulphur di-oxide ($SO_2$) | IS: 5182, Part 2-2001 | 14 | 6.6 | $\mu g/m^3$ | 53% |
| 4 | Nitrogen di-oxide ($NO_2$) | IS: 5182, Part 6-2006 | 11 | 4.73 | $\mu g/m^3$ | 57% |
| 5 | Ozone ($O_3$) | IS: 5182, Part 9 | 0.021 | 0.0234 | ppm | −11% |

Test 7:
Timing: 08:00 PM to 12:00 AM
Date: 3 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 200 | 64 | $\mu g/m^3$ | 68% |
| 2 | Particulate Matter ($PM_{2.5}$) | CPCB Guidelines, May 2011 | 80 | 31.2 | $\mu g/m^3$ | 61% |
| 3 | Sulphur di-oxide ($SO_2$) | IS: 5182, Part 2-2001 | 11 | 5 | $\mu g/m^3$ | 55% |
| 4 | Nitrogen di-oxide ($NO_2$) | IS: 5182, Part 6-2006 | 24 | 10 | $\mu g/m^3$ | 58% |
| 5 | Ozone ($O_3$) | IS: 5182, Part 9 | 0.02 | 0.0234 | ppm | −17% |

Test 8:
Timing: 06:00 AM to 06:00 PM
Date: 4 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 385 | 100 | $\mu g/m^3$ | 74% |
| 2 | Particulate Matter ($PM_{2.5}$) | CPCB Guidelines, May 2011 | 160 | 46.4 | $\mu g/m^3$ | 71% |
| 3 | Sulphur di-oxide ($SO_2$) | IS: 5182, Part 2-2001 | 25.9 | 9.8 | $\mu g/m^3$ | 62% |
| 4 | Nitrogen di-oxide ($NO_2$) | IS: 5182, Part 6-2006 | 40 | 14.4 | $\mu g/m^3$ | 64% |
| 5 | Ozone ($O_3$) | IS: 5182, Part 9 | 0.0354 | 0.0397 | ppm | −12% |

Test 9:
Timing: 07:00 PM to 07:00 AM
Date: 4-5 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 397 | 83.4 | $\mu g/m^3$ | 79% |
| 2 | Particulate Matter ($PM_{2.5}$) | CPCB Guidelines, May 2011 | 154 | 40 | $\mu g/m^3$ | 74% |
| 3 | Sulphur di-oxide ($SO_2$) | IS: 5182, Part 2-2001 | 21.7 | 7.7 | $\mu g/m^3$ | 65% |
| 4 | Nitrogen di-oxide ($NO_2$) | IS: 5182, Part 6-2006 | 46 | 14.7 | $\mu g/m^3$ | 68% |
| 5 | Ozone ($O_3$) | IS: 5182, Part 9 | 0.0356 | 0.039 | ppm | −10% |

Test 10:
Timing: 08:00 AM to 08:00 AM (24 hrs.)
Date: 5-6 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 109 | 15.2 | $\mu g/m^3$ | 86% |
| 2 | Particulate Matter ($PM_{2.5}$) | CPCB Guidelines, May 2011 | 43 | 8.2 | $\mu g/m^3$ | 81% |
| 3 | Sulphur di-oxide ($SO_2$) | IS: 5182, Part 2-2001 | 37 | 10.3 | $\mu g/m^3$ | 72% |
| 4 | Nitrogen di-oxide ($NO_2$) | IS: 5182, Part 6-2006 | 22 | 5 | $\mu g/m^3$ | 77% |
| 5 | Ozone ($O_3$) | IS: 5182, Part 9 | 0.034 | 0.0384 | ppm | −13% |

III] Test results for 12000 $m^3$/hr air purification system:
Test 1:
Timing: 08:00 AM to 10:00 AM
Date: 7 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 252 | 131 | $\mu g/m^3$ | 48% |
| 2 | Particulate Matter ($PM_{2.5}$) | CPCB Guidelines, May 2011 | 115 | 64.4 | $\mu g/m^3$ | 44% |
| 3 | Sulphur di-oxide ($SO_2$) | IS: 5182, Part 2-2001 | 2.9 | 1.7 | $\mu g/m^3$ | 40% |
| 4 | Nitrogen di-oxide ($NO_2$) | IS: 5182, Part 6-2006 | 27 | 15.9 | $\mu g/m^3$ | 41% |
| 5 | Ozone ($O_3$) | IS: 5182, Part 9 | 0.0104 | 0.0115 | ppm | −11% |

Test 2:
Timing: 01:00 PM to 03:00 PM
Date: 7 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 78 | 35.9 | $\mu g/m^3$ | 54% |
| 2 | Particulate Matter ($PM_{2.5}$) | CPCB Guidelines, May 2011 | 25 | 13.5 | $\mu g/m^3$ | 46% |
| 3 | Sulphur di-oxide ($SO_2$) | IS: 5182, Part 2-2001 | 4.2 | 2.5 | $\mu g/m^3$ | 41% |
| 4 | Nitrogen di-oxide ($NO_2$) | IS: 5182, Part 6-2006 | 13 | 7.2 | $\mu g/m^3$ | 45% |
| 5 | Ozone ($O_3$) | IS: 5182, Part 9 | 0.012 | 0.014 | ppm | −17% |

Test 3:
Timing: 04:00 PM to 06:00 PM
Date: 7 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 80 | 35.2 | $\mu g/m^3$ | 56% |
| 2 | Particulate Matter ($PM_{2.5}$) | CPCB Guidelines, May 2011 | 29 | 15 | $\mu g/m^3$ | 48% |
| 3 | Sulphur di-oxide ($SO_2$) | IS: 5182, Part 2-2001 | 5 | 2.8 | $\mu g/m^3$ | 43% |
| 4 | Nitrogen di-oxide ($NO_2$) | IS: 5182, Part 6-2006 | 13 | 6.6 | $\mu g/m^3$ | 49% |
| 5 | Ozone ($O_3$) | IS: 5182, Part 9 | 0.01 | 0.012 | ppm | −13% |

Test 4:
Timing: 07:00 PM to 09:00 PM
Date: 7 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 117 | 49.1 | $\mu g/m^3$ | 58% |
| 2 | Particulate Matter ($PM_{2.5}$) | CPCB Guidelines, May 2011 | 28 | 13.7 | $\mu g/m^3$ | 51% |
| 3 | Sulphur di-oxide ($SO_2$) | IS: 5182, Part 2-2001 | 2 | 1.1 | $\mu g/m^3$ | 45% |
| 4 | Nitrogen di-oxide ($NO_2$) | IS: 5182, Part 6-2006 | 43 | 21.07 | $\mu g/m^3$ | 51% |
| 5 | Ozone ($O_3$) | IS: 5182, Part 9 | 0.013 | 0.0128 | ppm | −13% |

Test 5:
Timing: 08:00 AM to 12:00 PM
Date: 8 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 180 | 73.8 | $\mu g/m^3$ | 59% |
| 2 | Particulate Matter ($PM_{2.5}$) | CPCB Guidelines, May 2011 | 84 | 40.3 | $\mu g/m^3$ | 52% |
| 3 | Sulphur di-oxide ($SO_2$) | IS: 5182, Part 2-2001 | 8.2 | 4.7 | $\mu g/m^3$ | 43% |
| 4 | Nitrogen di-oxide ($NO_2$) | IS: 5182, Part 6-2006 | 45 | 23.4 | $\mu g/m^3$ | 48% |
| 5 | Ozone ($O_3$) | IS: 5182, Part 9 | 0.021 | 0.023 | ppm | −10% |

Test 6:
Timing: 02:00 PM to 6:00 PM
Date: 8 Mar. 2018

| No. | Parameter | Method Protocol | Near air purifier inlet | Near air purifier outlet | Unit | Removal Efficiency |
|---|---|---|---|---|---|---|
| 1 | Particulate Matter (PM$_{10}$) | IS: 5182, Part 23-2006 | 154 | 52.4 | µg/m$^3$ | 66% |
| 2 | Particulate Matter (PM$_{2.5}$) | CPCB Guidelines, May 2011 | 69 | 28.3 | µg/m$^3$ | 59% |
| 3 | Sulphur di-oxide (SO$_2$) | IS: 5182, Part 2-2001 | 14 | 7.8 | µg/m$^3$ | 44% |
| 4 | Nitrogen di-oxide (NO$_2$) | IS: 5182, Part 6-2006 | 26 | 13.5 | µg/m$^3$ | 48% |
| 5 | Ozone (O$_3$) | IS: 5182, Part 9 | 0.021 | 0.0234 | ppm | −11% |

Test 7:
Timing: 08:00 PM to 12:00 AM
Date: 8 Mar. 2018

| No. | Parameter | Method Protocol | Near air purifier inlet | Near air purifier outlet | Unit | Removal Efficiency |
|---|---|---|---|---|---|---|
| 1 | Particulate Matter (PM$_{10}$) | IS: 5182, Part 23-2006 | 245 | 78.4 | µg/m$^3$ | 68% |
| 2 | Particulate Matter (PM$_{2.5}$) | CPCB Guidelines, May 2011 | 106 | 42.4 | µg/m$^3$ | 60% |
| 3 | Sulphur di-oxide (SO$_2$) | IS: 5182, Part 2-2001 | 11 | 5.7 | µg/m$^3$ | 48% |
| 4 | Nitrogen di-oxide (NO$_2$) | IS: 5182, Part 6-2006 | 57 | 27.9 | µg/m$^3$ | 51% |
| 5 | Ozone (O$_3$) | IS: 5182, Part 9 | 0.02 | 0.0234 | ppm | −17% |

Test 8:
Timing: 06:00 AM to 06:00 PM
Date: 9 Mar. 2018

| No. | Parameter | Method Protocol | Near air purifier inlet | Near air purifier outlet | Unit | Removal Efficiency |
|---|---|---|---|---|---|---|
| 1 | Particulate Matter (PM$_{10}$) | IS: 5182, Part 23-2006 | 186 | 27.9 | µg/m$^3$ | 85% |
| 2 | Particulate Matter (PM$_{2.5}$) | CPCB Guidelines, May 2011 | 88 | 18.5 | µg/m$^3$ | 79% |
| 3 | Sulphur di-oxide (SO$_2$) | IS: 5182, Part 2-2001 | 26 | 10.1 | µg/m$^3$ | 61% |
| 4 | Nitrogen di-oxide (NO$_2$) | IS: 5182, Part 6-2006 | 24 | 8.4 | µg/m$^3$ | 65% |
| 5 | Ozone (O$_3$) | IS: 5182, Part 9 | 0.0354 | 0.0397 | ppm | −12% |

Test 9:
Timing: 07:00 PM to 07:00 AM
Date: 9-10 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 111 | 14.4 | $\mu g/m^3$ | 87% |
| 2 | Particulate Matter ($PM_{2.5}$) | CPCB Guidelines, May 2011 | 52 | 9.9 | $\mu g/m^3$ | 81% |
| 3 | Sulphur di-oxide ($SO_2$) | IS: 5182, Part 2-2001 | 22 | 8.1 | $\mu g/m^3$ | 63% |
| 4 | Nitrogen di-oxide ($NO_2$) | IS: 5182, Part 6-2006 | 34 | 10.9 | $\mu g/m^3$ | 68% |
| 5 | Ozone ($O_3$) | IS: 5182, Part 9 | 0.0356 | 0.039 | ppm | −10% |

Test 10:
Timing: 08:00 AM to 08:00 AM
Date: 10-11 Mar. 2018

| No. | Parameter | Method Protocol | Near air purifier inlet | Near air purifier outlet | Unit | Removal Efficiency |
|---|---|---|---|---|---|---|
| 1 | Particulate Matter ($PM_{10}$) | IS: 5182, Part 23-2006 | 129 | 18 | $\mu g/m^3$ | 86% |
| 2 | Particulate Matter ($PM_{2.5}$) | CPCB Guidelines, May 2011 | 51 | 8.7 | $\mu g/m^3$ | 83% |
| 3 | Sulphur di-oxide ($SO_2$) | IS: 5182, Part 2-2001 | 37 | 9.6 | $\mu g/m^3$ | 74% |
| 4 | Nitrogen di-oxide ($NO_2$) | IS: 5182, Part 6-2006 | 23 | 5.3 | $\mu g/m^3$ | 77% |
| 5 | Ozone ($O_3$) | IS: 5182, Part 9 | 0.034 | 0.0384 | ppm | −13% |

From the aforementioned set of tabulated results, it is inferred that, the efficiency of removal of $PM_{2.5}$ of the air purification system of the present disclosure ranges from 40% to 80% and above. At the same time, the removal efficiency for $PM_{10}$, $SO_2$ and $NO_2$ ranges from 40% to nearly 80% removal efficiency.

When an element is referred to as being "mounted on", "engaged to", "connected to" or "coupled to" another element, it may be directly on, engaged, connected or coupled to the other element. As used herein, the term "and/or" includes any and all combinations of one or more of the associated listed elements.

The terms first, second, third, etc., should not be construed to limit the scope of the present disclosure as the aforementioned terms may be only used to distinguish one element, component, region, layer or section from another component, region, layer or section. Terms such as first, second, third etc., when used herein do not imply a specific sequence or order unless clearly suggested by the present disclosure.

Terms such as "inner", "outer", "beneath", "below", "lower", "above", "upper" and the like, may be used in the present disclosure to describe relationships between different elements as depicted from the figures.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

Technical Advancements

The present disclosure described herein above has several technical advantages including, but not limited to, the realization of an air purification system, which:

filters fine particles and coarse particles from the air;
 removes the suspended particles from the air;
 reduces gases such as $NO_x$, $SO_x$, $H_2S$ and odour emitted from chimney smoke, industrial emissions, traffic emissions and domestic emissions including central heating;
 maintains the levels of ozone within permissible limits in the purified air by bringing the levels of ozone generated, if any, within the purification system within permissible limits; and
 is economical.

The foregoing disclosure has been described with reference to the accompanying embodiments which do not limit the scope and ambit of the disclosure. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. An air purification system comprising:
   a. a tubular shell defined by at least one electrically grounded wall defined by an inner surface and an outer surface, an inlet and an outlet;
   b. a blower configured to generate flow of air through said tubular shell;
   c. at least one elongated electrode fitted within said tubular shell between said inlet and said outlet and electrically isolated from said tubular shell;
   d. an electric voltage supply configured to apply an electric current of a predetermined voltage on the at least one elongated electrode; and
   e. a plurality of spikes extending from said at least one elongated electrode, said spikes having tips spaced apart from said inner surface and configured to generate a corona between said tips and said inner surface when an electric current of high voltage is made to pass through said at least one elongated electrode and thereby ionize gases and charge particles present in the air resulting in said charged particles being deposited on said inner surface of said tubular shell;
   wherein a predetermined distance of separation between said plurality of spikes varies along the length of said at least one elongated electrode, and wherein said predetermined distance of separation between said plurality of spikes decreases along the length of said at least one elongated electrode towards said outlet of said shell.

2. The air purification system as claimed in claim 1, wherein said plurality of spikes are provided along the length of said at least one elongated electrode in a spatially distributed manner.

3. The air purification system as claimed in claim 1, wherein said at least one elongated electrode is an elongated strip of conductive material, wherein said plurality of spikes are formed on at least one edge of said elongated strip, and said elongated strip is twisted along its length through a predetermined angle with number of twists based on the length of the at least one elongated electrode, thereby forming a dual-helical corona there around when an electric current of high voltage is made to pass through said at least one elongated electrode.

4. The air purification system as claimed in claim 1, wherein said at least one elongated electrode is an elongated strip of conductive material, wherein said plurality of spikes are externally attached on at least one edge of said elongated strip, and said elongated strip is twisted along its length through a predetermined angle with number of twists based on the length of the at least one elongated electrode, thereby forming a dual-helical corona there around when an electric current of high voltage is made to pass through said at least one elongated electrode.

5. The air purification system as claimed in claim 1, wherein said at least one elongated electrode is formed from a tube of conductive material by attaching said plurality of spikes on said tube.

6. The air purification system as claimed in claim 1, wherein said at least one elongated electrode is formed from a rod of conductive material by attaching said plurality of spikes on an external surface of said rod.

7. The air purification system as claimed in claim 1, wherein said plurality of spikes are arranged in a spaced apart configuration.

8. The air purification system as claimed in claim 5, wherein a cross-section of said tube is selected from the group consisting of circular, oval, elliptical, regular polygonal and irregular polygonal.

9. The air purification system as claimed in claim 6, wherein a cross-section of said rod is selected from the group consisting of circular, oval, elliptical, regular polygonal and irregular polygonal.

10. The air purification system as claimed in claim 1, wherein said tubular shell comprises a plurality of electrodes and a plurality of internal walls defining a plurality of chambers with one chamber enclosing each electrode.

11. The air purification system as claimed in claim 1, wherein said system comprises a pre-filtration chamber.

12. The air purification system as claimed in claim 1, wherein said system comprises a post-filtration chamber.

13. The air purification system as claimed in claim 1, wherein velocity of flow of air is in the range of 1 m/s to 7 m/s.

14. The air purification system as claimed in claim 3, wherein said number of twists across the at least one elongated electrode based on the length of said at least one electrode are at a predetermined angle in the range of 5° to 720°.

15. The air purification system as claimed in claim 1, wherein said predetermined voltage is in the range of 25000V to 50000V.

16. The air purification system as claimed in claim 1, wherein said predetermined voltage is in the range of 3000V to 15000V.

* * * * *